(12) United States Patent
Belfor et al.

(10) Patent No.: US 7,357,635 B2
(45) Date of Patent: *Apr. 15, 2008

(54) SYSTEM AND METHOD TO BIOENGINEER FACIAL FORM IN ADULTS

(75) Inventors: Theodore Belfor, Catskill, NY (US); Gurdev Dave Singh, San Juan, PR (US)

(73) Assignee: Orthovisage Inc., Catskill, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/132,136

(22) Filed: May 18, 2005

(65) Prior Publication Data

US 2005/0260534 A1  Nov. 24, 2005

Related U.S. Application Data

(63) Continuation-in-part of application No. 10/849,713, filed on May 19, 2004.

(51) Int. Cl.
*A61C 7/00* (2006.01)
*A61F 5/042* (2006.01)
*A61F 5/08* (2006.01)

(52) U.S. Cl. .............................. 433/24; 433/7; 606/58
(58) Field of Classification Search .................... 433/7, 433/18, 19, 21, 24; 600/589, 600; 606/57, 606/58, 90

See application file for complete search history.

(56) References Cited

U.S. PATENT DOCUMENTS

| 4,026,023 | A | * | 5/1977 | Fisher | 433/7 |
| 4,239,487 | A | * | 12/1980 | Murdock | 433/7 |
| 4,433,956 | A | * | 2/1984 | Witzig | 433/7 |
| 4,439,149 | A |   | 3/1984 | Devincenzo | |
| 4,457,708 | A |   | 7/1984 | Dufour | |
| 4,609,349 | A | * | 9/1986 | Cain | 433/6 |
| 5,002,485 | A | * | 3/1991 | Aagesen | 433/7 |
| 5,163,840 | A |   | 11/1992 | Bourke | |

(Continued)

*Primary Examiner*—Cary E. O'Connor
(74) *Attorney, Agent, or Firm*—Hoffman, Warnick & D'Alessandro LLC

(57) ABSTRACT

A method and apparatus are provided for changing the form of the jaw and facial bones of an adult patient that did not develop fully during childhood. The method utilizes a device having a plate body with an expansion screw that fits within the mouth of the patient; flap springs that project from the plate body, and an overlay extending from the plate body. The device is placed within the mouth of the patient so that the overlay is in a position between at least two opposing teeth. In this position, opposing teeth contact the overlay during function (e.g. swallowing). This intermittent, unilateral application of force to the facial bones causes these bones to further develop, positioning out of place teeth into more proper positions, and inducing a more symmetrical and enhanced appearance of the face, as well as increasing the airway space behind the jaws. Concomitantly, the flap springs gently press against selected teeth that are out of alignment in order to guide those teeth into place. Simultaneously, the expansion device maintains these forces on the teeth, while assisting the jawbones to expand to accept the teeth in their proper position. The expansion device can be adjusted by small motors under the control of a microprocessor located on the body plate based on readings from sensors on the flap springs. The expansion device can be adjusted by remote signaling, using a global position satellite technology and global position coordinates.

23 Claims, 16 Drawing Sheets

U.S. PATENT DOCUMENTS

| | | |
|---|---|---|
| 5,324,196 A | 6/1994 | Magill |
| 5,334,202 A * | 8/1994 | Carter .................. 606/58 |
| 5,443,384 A | 8/1995 | Franseen et al. |
| 5,536,168 A | 7/1996 | Bourke |
| 5,795,150 A | 8/1998 | Boyd |
| 5,848,891 A | 12/1998 | Eckhart et al. |
| 5,848,981 A | 12/1998 | Herbranson |
| 6,096,079 A | 8/2000 | Eaton |
| 6,099,304 A | 8/2000 | Carter |
| 6,113,599 A * | 9/2000 | Landsberger .......... 606/60 |
| 6,334,771 B1 | 1/2002 | Liou |
| 6,435,870 B1 | 8/2002 | Walde |
| 6,530,375 B1 | 3/2003 | Cieslik, Jr. |
| 6,604,527 B1 | 8/2003 | Palmisano |
| 6,648,639 B2 | 11/2003 | Mao |
| 2002/0072029 A1* | 6/2002 | Mao ..................... 433/24 |
| 2003/0049581 A1* | 3/2003 | DeLuke ................. 433/7 |
| 2004/0009449 A1 | 1/2004 | Mah et al. |
| 2004/0013993 A1 | 1/2004 | Ito |
| 2005/0186524 A1* | 8/2005 | Abolfathi et al. ......... 433/7 |

* cited by examiner

SYSTEM AND METHOD TO BIOENGINEER FACIAL FORM IN ADULTS

CROSS-REFERENCE TO RELATED APPLICATIONS

This application is a continuation-in-part of co-pending U.S. patent application Ser. No. 10/849,713, filed May 19, 2004, pending which is hereby incorporated herein.

BACKGROUND OF THE INVENTION

1. Field of the Invention

The present invention relates to a non-surgical method to enhance facial form and facial symmetry by using an orthodontic dental device or appliance in adults. More specifically, the present invention relates to an orthodontic device that stimulates the genes of the face and jaws, which in turn stimulate the bone causing a remodeling or reshaping that improves facial symmetry and causes jaw development where jaw development did not occur during childhood, with subsequent physiologic enhancements.

2. Discussion of the Related Art

Devices have been used for decades to straighten patients' teeth. Patients' teeth may not erupt optimally for a number of reasons, specifically if the jawbone did not fully develop during childhood. Thus, in an underdeveloped jaw there is not sufficient room to accommodate the patient's full set of teeth. Because there is not enough room in the jawbone for all of a patient's teeth, some of these devices first require extraction of one or more teeth to provide room in the patient's jaws for the remaining teeth, so that they may be rotated or otherwise moved into a straighter position.

One conventional device that is used to straighten the alignment of teeth is braces. Braces are used to move teeth, which causes the bone to change locally around the roots of the teeth. Braces do not, however, stimulate the muscles of the face and/or jaws, and, therefore, do not cause any change of the facial bones or jaw bones, except for the local change of the jawbone around the roots of the teeth moved by the braces.

Another device used to straighten the alignment of teeth is a split palate orthodontic appliance such as that disclosed in U.S. Pat. No. 4,026,023 of Fisher. Split palate appliances include a split acrylic body whose two body halves are connected with an expansion screw. The acrylic body rests against the palate of the mouth when the device is placed in the upper jaw, or against the lingual surfaces of the mandible when the device is placed in the lower jaw. Because prior split palate devices contact the palate, they prevent the palate from descending as the palate is widened. T-shaped flap springs, which are also known as Fisher flap springs, are embedded in the plate body. The free edge of each spring makes contact with a selected tooth or teeth to apply a predetermined amount of pressure against that tooth. This pressure slowly causes selective orthodontic movement of the teeth. In particular, the pressure applied by the springs to the teeth slowly decreases due to changes in the palate or mandible caused by the pressure. Thus, periodically (once or twice a week) the expansion screw is actuated to further spread apart the two body halves, thereby applying (or more accurately reapplying) more pressure against the respective teeth. As the jaw remodels, however, the widening is usually limited inter alia by sutural homeostasis, a regulatory mechanism that is under genetic control, and modulated in response to function.

Remodeling of bone through force can occur throughout a person's life. It is believed that the bones of some individuals do not fully develop during childhood because of a lack of sufficient stimulation. Primitive man had better-developed jaws, straighter teeth and a wider smile than his modern day descendants, because of exclusive breast-feeding during infancy. As well, the food was very tough and a baby would eat the same food as the parents. Modern day babies are often not breast-fed, are bottle-fed, may use pacifiers and are often reared on soft foods so their jaws do not develop as well. On top of that, these changes in feeding behavior and/or environmental pollution narrow the nasal passages of many post-industrial infants. As a result they breathe through their mouth, causing their palate to develop inward instead of outward, and leaving less room for their upper teeth. Not only does this result in crowded and crooked teeth, but a lack of lower jaw development also affects the overall morphology of the face.

There is a direct relationship between facial development and beauty. In every culture of the world, a symmetrical face with high cheekbones, a wide smile and a strong jaw is considered beautiful. It is now known that infants will respond to a wide beautiful smile with even teeth. Adults also respond to a well-developed face and body as being beautiful.

In the article by Moss, "The role of mechanotransduction," *American Journal of Orthodontics Dentofacial Orthopedics*, 112:8-11 (1997) there is a discussion of the "functional matrix hypothesis." It asserts that a seamless communication takes place when mechanical forces load the periosteum (tissues around the bone and teeth). In effect there is a cascade of mechanical/biochemical communications that takes place all the way down to the individual gene-containing nucleus of the cells that synthesize bone, reside in bone and direct changes in bone. These communications affect the DNA of the genome within the nucleus of undifferentiated mesenchymal cells (similar to adult stem cells) and create an interconnected sequence of molecular events. Thus, the periosteal functional matrix, which regulates the genomic activity of its strained skeletal unit bone cells, including their phenotypic expression, is activated. Therefore, the theory is that the strain placed on the bone induces the bone to change via mechanotransduction, and triggers the genetic encoding of the bone via sutural homeostasis to cause it to continue its earlier arrested development toward a symmetrical facial appearance, by evoking dormant or unexpressed genes in non-growing adults.

Recent studies in laboratory animals such as rabbits and rats have conclusively shown that facial sutures respond to mechanical stimuli by gene expression, and that altered jaw position using a physical device also evokes gene expression in the jaw. Because of the homology of the human and mammalian genomes of the craniofacial region (i.e. the Homeobox genes), it is reasonable to predicate facial development in patients using a device of the present invention on similar molecular genetic developmental mechanisms.

None of the prior art devices directly stimulates the genes of the face and jaws, which in turn stimulate the bone causing a remodeling or reshaping of the facial bones and jaw bones to improve facial symmetry.

None of the prior art devices causes the jawbones to develop where jaw development did not occur during childhood.

SUMMARY OF THE INVENTION

The present invention is directed to a method for changing a craniofacial feature of an individual, particularly the form of the jaw and facial bones of an adult patient that did not develop fully during childhood, by intermittently applying force to the bones through a device that translates the functional actions of the patient, such as swallowing, into the necessary signal, allied with spatial changes associated with the overlay of the appliance/device.

In accordance with a presently preferred exemplary embodiment of the present invention, the method utilizes a device or appliance having a plate body that fits within the mouth of the patient. The plate may be in two halves connected by an expansion screw. Flap springs project from the plate body and an overlay extends from the plate body. Clasps with archways are also connected to the plate.

In practicing the method, the appliance is placed within the mouth of the patient, e.g., at night. It can be shaped to fit either the lower jaw (mandible) or upper jaw (maxilla) or both jaws simultaneously. In any case, the archway of each clasp is selectively placed about a tooth to hold the appliance in place. In this position the overlay extends over a tooth and prevents the jaws from fully closing. Initially, the overlay is placed on the patient's underdeveloped side. The flap springs gently press against selected teeth that are out of alignment in order to guide those teeth into place. The unilateral vectors of force on the tooth's periodontium cause the jawbone to expand and (eventually) accept the teeth in their proper position, in accord with the developmental mechanisms of sutural homeostasis. Also, the device is arranged such that it does not contact the palate and this small space is normally occupied by saliva. When the patient swallows, a relative decrease in pressure occurs between the palate and the base plate of the appliance. This pressure differential exerts tension intermittently on the facial bones via the palatal tissues during swallowing. This intermittent application of force to the facial bones causes these bones to further develop toward a symmetrical appearance of the face, and also help position out of place teeth into proper positions. On the other side of the mouth, the opposing teeth do not make contact due to the overlay. These decreased unilateral vectors of force on the tooth's periodontium cause the jawbone to develop (supra-eruption) but the expansion device takes advantage of this phenomenon by remodeling the jaws in a transverse rather than vertical direction, so that eventually, the teeth are accepted in a more proper position, in accord with the developmental mechanisms of mechanotransduction. Thus, it is believed that the development of the bones into a symmetrical shape is due to the functional matrix effect.

The plate body halves of the device can be adjusted toward or away from each other by a small micro-motor connected to, or embodying the expansion screw. Further, the position of the flap springs, and thus the force they apply to the teeth, can also be adjusted by the same motor due to the movement of the body halves, or by one or additional micro-motors attached to the flap springs. Sensors may be applied to the flap springs so that the amount of force applied by these springs, either because of their motor or the separation of the body plate halves, can be determined. Further, a global positioning coordinate system can be incorporated into the device. Further, a microprocessor can be located on the body plate and used to interpret the sensor readings and global positioning coordinates. Further, the microprocessor can adjust the expansion screw motor and/or the flap spring motors based on the sensor readings, e.g., to keep the pressure even. Further, the dental health care professional can design a force pattern to be applied by the device to achieve the desired results. This pattern can be stored as predetermined parameters in a memory associated with the microprocessor, and used by the microprocessor with the sensor readings to adjust the motor or motors. Further, a dental health care provider can use remote signaling to control the device using any wireless signal protocols known in the art.

A first aspect of the invention provides a method for changing in an individual at least one craniofacial feature selected from a group consisting of an osteological feature, a dental feature, an anatomical feature, or a cosmetic feature, the method comprising the steps of providing a device having a plate body that fits within the mouth of the individual, a flap spring that projects from the plate body, and an overlay extending from the plate body, placing the device within the mouth of the individual so that the overlay is in a position between at least an upper and lower tooth of the individual, the flap spring presses against at least one selected tooth that is out of place, and the plate body is spaced from the individual's tissues, including the palate, and arranging the shape and placement of the device such that contact of the individual's upper tooth and lower tooth or teeth with the overlay causes the individual's facial muscles to intermittently pull on at least one facial bone when the individual swallows, thereby causing a change in a craniofacial feature.

A second aspect of the invention provides a device for affecting a change in a craniofacial feature of an individual, the device comprising a plate body having two halves and adapted to fit within the individual's mouth, an overlay extending from at least one of the plate body halves and adapted to fit between at least one upper tooth and at least one opposing lower tooth and prevent the individual's mouth from fully closing, a clasp connected to the plate body and adapted to connect the device to at least one tooth, and an expansion screw for adjusting a distance between the plate body halves.

A third aspect of the invention provides a system for changing in an individual at least one craniofacial feature, the system comprising a device adapted to affect a change in at least one craniofacial feature of the individual, wherein the device includes a positioner for adjusting the device and a sensor for collecting data from the devices, a device control system, wherein the device control system includes a sensory system configured to receive data generated by the sensor and a positioning system for generating position instructions for the positioner.

A fourth aspect of the invention provides a method for changing in an individual at least one craniofacial feature, the method comprising the steps of providing a device for affecting a change in the at least one craniofacial feature, wherein the device is capable of measuring at least one of a pressure applied to a tooth of an individual and a distance between a first portion and a second portion of the device, providing a device control system, sending measurement data from the sensor to the device control system, and sending positional data from the device control system to the device for altering at least one of the pressure applied to the tooth of an individual and the distance between the first portion and the second portion of the device.

BRIEF DESCRIPTION OF THE DRAWINGS

These and other features, aspects, and advantages of the present invention will become better understood with reference to the following description, appended claims and the accompanying drawings wherein:

DETAILED DESCRIPTION

Figure 1:
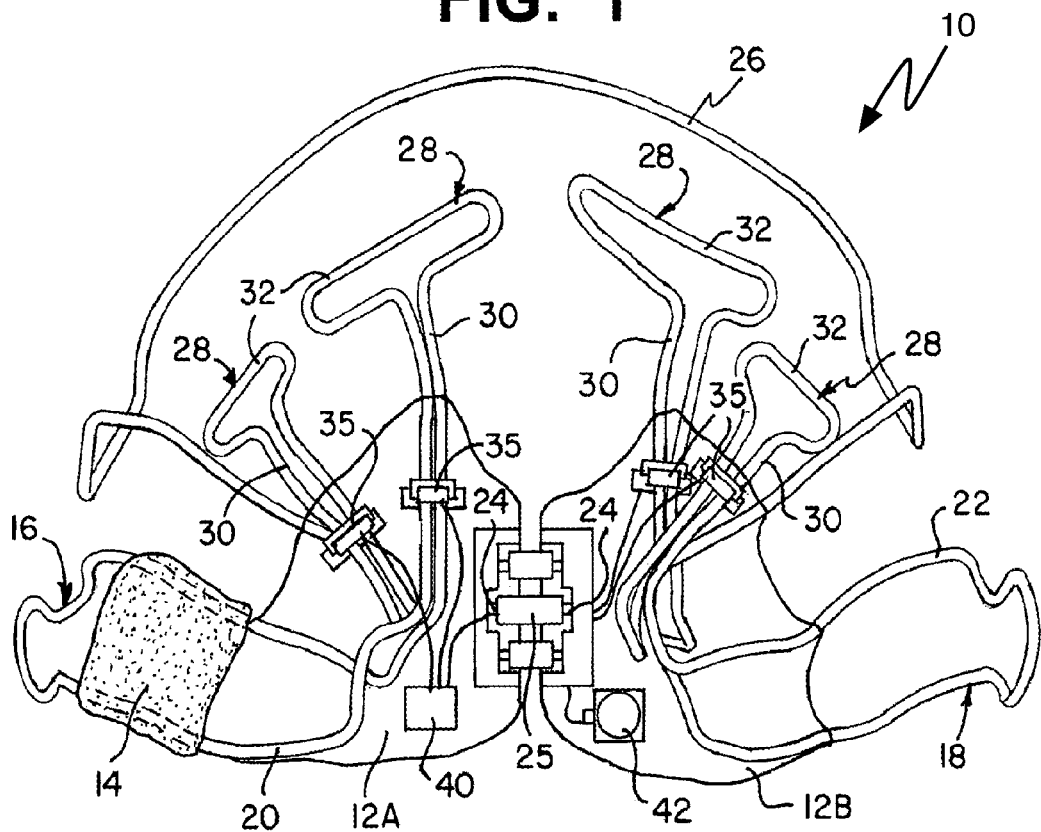
FIG. 1 is a top plan view of a device in accordance with the present invention.
Figure 2:
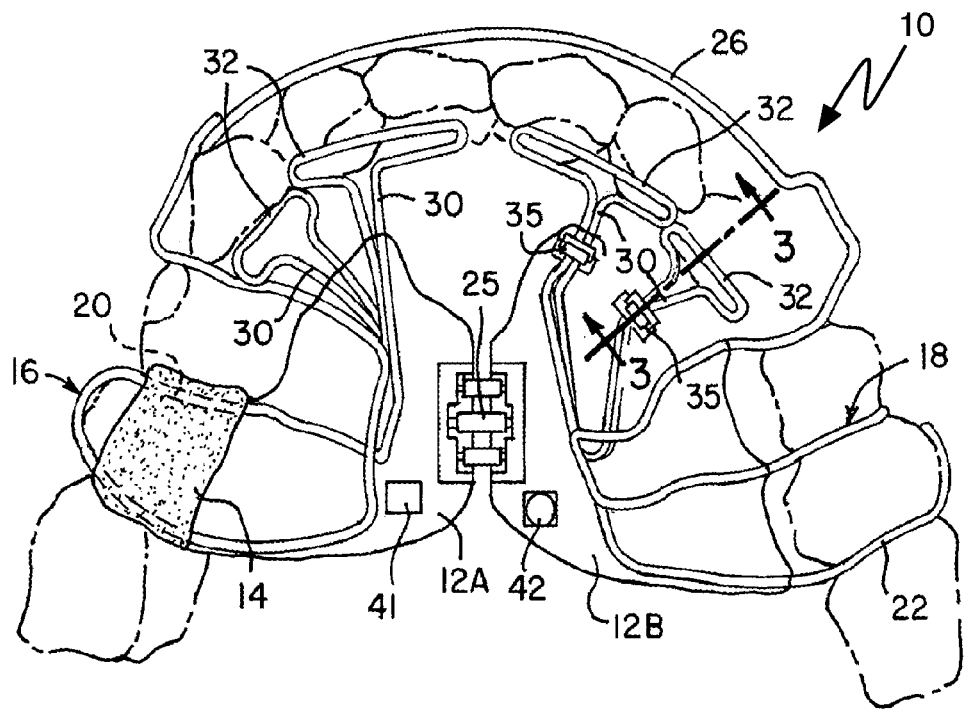
FIG. 2 is a top plan view of a device in accordance with the present invention, which is located in conjunction with the upper teeth of a patient at the beginning of treatment and may be used to develop the jawbone and facial bones, and align the teeth of the patient.
Figure 3:
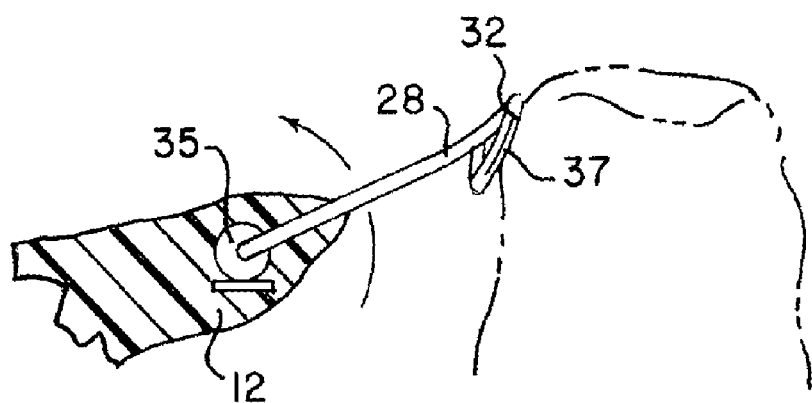
FIG. 3 is a cross-sectional view of the device of FIG. 2 along line 2-2.

Referring to FIGS. 1-3, there is shown an orthodontic device or appliance 10 of the split palate type in accordance with the present invention. Device 10 includes a plate body 12, preferably of plastic material, such as acrylic. The plate body is preferably in two halves 12A, 12B, but it can be in one piece or in several pieces of unequal size. Plate body 12 has an overlay 14 extending from it to a position that would cover the top of a tooth. While it is shown with one such overlay 14 on the left side in FIG. 1, it should be understood that the overlay may be on the right side and/or the left side. The location of the overlay is based on a clinical determination by the dental health care provider as to which functional matrices should be activated more to achieve the desired result in an optimal way or how much stress should be applied. Typically more stress is applied to the functional matrices on the side where the overlay is located. As a result the overlay should be on the side where the facial and jawbones did not fully develop during childhood. Additionally, multiple overlays including more than one on each side of the device may be used.

A first clasp 16 and a second clasp 18 are connected to the plate, preferably by being embedded in the plastic material of plate body 12. Each clasp 16, 18 includes an archway 20, 22 for selectively permitting device 10 to be fitted about a tooth, preferably one of the posterior teeth, to hold the device or appliance in place. When fitted or connected, overlay 14 may be positioned to extend over one of the archways (archway 20 is shown in the FIG. 1, but overlay 14 could additionally or alternatively extend over archway 22) so as to be in contact with the tooth. Overlay 14 is preferably placed on top of the tooth adjacent to the archway 20 or 22 of the respective clasp 18, 20, thereby preventing the jaw from fully closing.

The halves 12A, 12B of plate body 12 may be connected by an expansion jack screw 24. While the screw 24 may be manually adjustable to control the separation of the plate halves, a small electrical micro-motor 25 may incorporate the screw 24 and be used to adjust the separation.

A Hawley frame 26, in the form of a labial bow arch wire, is also connected to the plate body 12, preferably by being embedded in the plastic material of the plate body 12. Hawley frame 26 wraps around the front of the teeth, acts as a lip bumper, prevents unwanted proclination of teeth, and additionally acts to keep the device 10 in place.

A plurality of flap springs 28, which are known in the art as Fisher flap springs, are connected to the plate body, preferably by being embedded in the plastic material of the plate body 12. Each flap spring is T-shaped, I-shaped or L-shaped including a tag portion 30 and a tooth supporting portion 32. Some of the tooth supporting portions 32 extend for a distance equal to at least the width of two teeth (see FIGS. 2 and 3). As is common, the tooth support portion 32 rests against the inside of the teeth and applies gentle pressure at that location. Typically, the amount of pressure can be adjusted by manual bending of the tag portions 30.

As an alternative, small electrical motors 35 can be located between the body plate 12 and one or more of the flap springs 28. These small electrical motors 35 adjust the separation of the two plate halves automatically without having to manually turn the expansion screw, and may additionally adjust the pressure that the flap springs apply to the teeth without having to manually bend the springs. In addition, sensors 37 can be located at the ends of the flap springs where they meet the teeth in order to measure the pressure applied to each tooth or group of teeth by the flap spring. The sensor 37 can be located in other positions, but in such a case it would not provide a direct measurement of the pressure and some calculation would be necessary to arrive at the actual pressure. In an alternate embodiment, one or more sensors 37 may be a global positioning device used to monitor changes in tooth position.

During use of the device, as the jaw expands and other bones develop, it will be necessary to adjust the separation of the body plates 12A, 12B, as well as the force of the flap springs, in order to continue the development of the bones. Adjustment of the separation of the body plates 12A, 12B can be accomplished by the patient turning the jack screw e.g., once a week. Adjustment of the force of the flap springs can be accomplished during periodic (e.g., once every three to four weeks) visits to the dental health care provider. Such adjustments can be manual or, where the motors 25, 35 are present, they can be made by applying an electric current to the motors. In part, these adjustments by the dental health care provider can be assisted by the provider reading the output of sensors 37, one or more of which may be a global positioning device.

A microprocessor 40 can be provided on or embedded within the body plate 12. In order to power the microprocessor, a battery 42 would also be provided. The microprocessor may be supplied via conducting wires with information from the sensors 37 and its output can drive the micro-motors 25, 35, via other conducting wires at least partially embedded in the plastic body 12, in order to automatically keep the pressure on the teeth at a preset level. In this way patient errors such as missed, over-zealous or reversed screw-turns are eliminated, and the visits to the dental health care provider are reduced to an optimized level. Further, the dental heath care provider can create a force profile that will lead to a good outcome for the patient. For example, the force vectors need to be intermittent, long-acting, low-level, and consistent so as not to over do the application of force and produce an inferior result. This profile may be in the form of data or digital codes stored in a memory that is part of the microprocessor. Thus the microprocessor would control the motors based on the profile data and the readings from the sensors.

By definition, the plate body 12 does not include the clasps 16, 18, the Hawley frame 26 and the flap springs 28. The body 12 of device 10, except for the overlay 14, is spaced from the patient's tissues, including the palate and mandibular lingual areas. Therefore, the only portion of the plate body 12 that touches the patient's tissue is the overlay 14, which contacts the biting (occlusal) surface of at least one of the patient's teeth in the space where that tooth would normally contact an opposing tooth from the opposite set of teeth, i.e., upper or lower jaw. Overlay 14 is sufficiently thick to prevent the jaws from fully closing. The thickness of the overlay where it contacts the tooth preferably ranges from approximately 0.5 mm to approximately 6.0 mm. More preferably, the overlay has a thickness ranging from approximately 1.0 mm to approximately 5.0 mm. Most preferably, the thickness of the overlay ranges from approximately 2.0 mm to approximately 4.0 mm, with about 2.0 mm being preferred. The plate body 12 itself has a thickness that varies and ranges from about 2.0 mm to about 6.0 mm.

To change the form of the jaw and facial bones with device 10, the device is placed within the mouth of a patient so that overlay 14 contacts at least one tooth and the remainder of the plate body 12 is spaced from the patient's tissue, including the palate. Overlay 14 prevents the patient's jaws from fully closing. This contact of the teeth with the overlay causes intermittent force to be applied to the body plate 12 and through it to the flap springs 28 to the teeth. It further causes the patient's jaw and facial muscles to stimulate the genes of facial and alveolar bones during function, essentially each time the patient swallows, which is estimated to be about 2,000 to 3,000 times per day. This frequent, intermittent signaling of the facial and alveolar bones is believed to cause development of the facial and jaw bones where jaw development did not fully occur during childhood. This bone development may include a descent of the palate (i.e., remodeling of the vault of the palate downwardly toward the lower jaw), and/or slight supra-eruption on the contra-lateral side to the unilateral bite block, if necessary, allied with bony remodeling of the midface upwards and outwards, according to the patient's genome.

Figure 4:
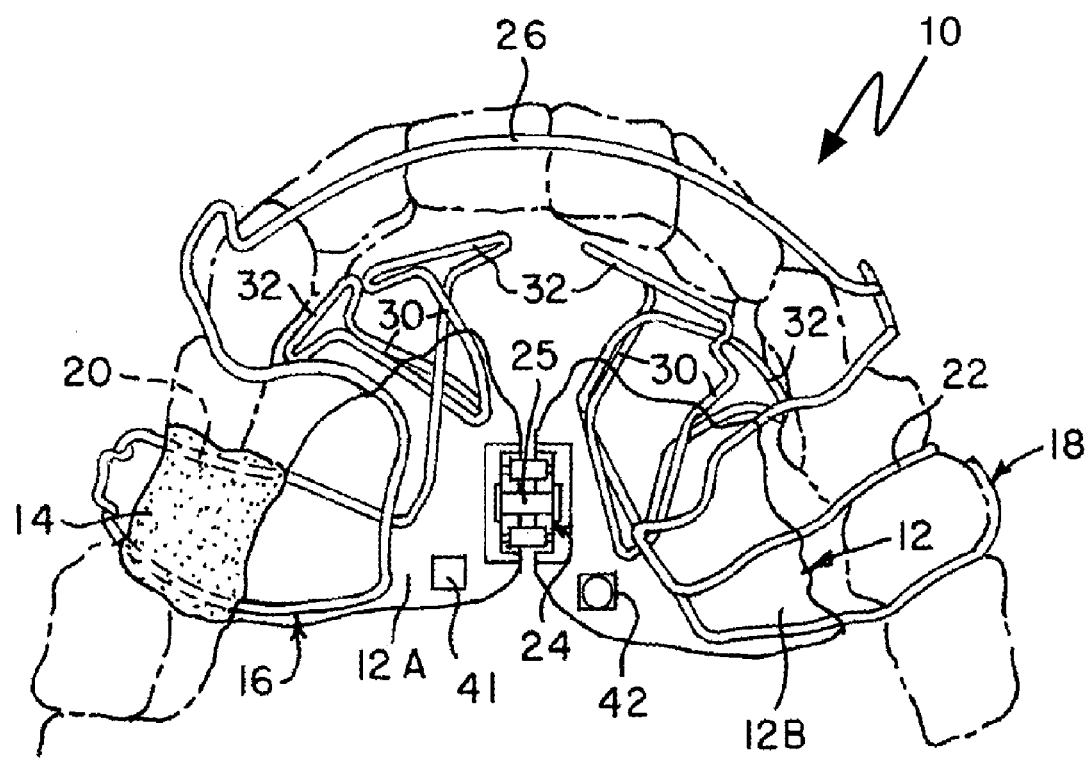
FIG. 4 is a top plan view of the device of FIG. 2 placed in the patient's mouth after partial treatment.

Assuming FIG. 2 shows the device of the present invention when initially used with a patient at the beginning of treatment, FIG. 4 is the same view of the device 10 after partial treatment. It should be noted that the teeth have been relocated outwardly in FIG. 4 compared to that in FIG. 2. In effect, the jawbone has been expanded to accommodate the new position of the teeth, without any spacing occurring between the teeth, unlike other devices used for maxillary expansion in children.

Figure 5:
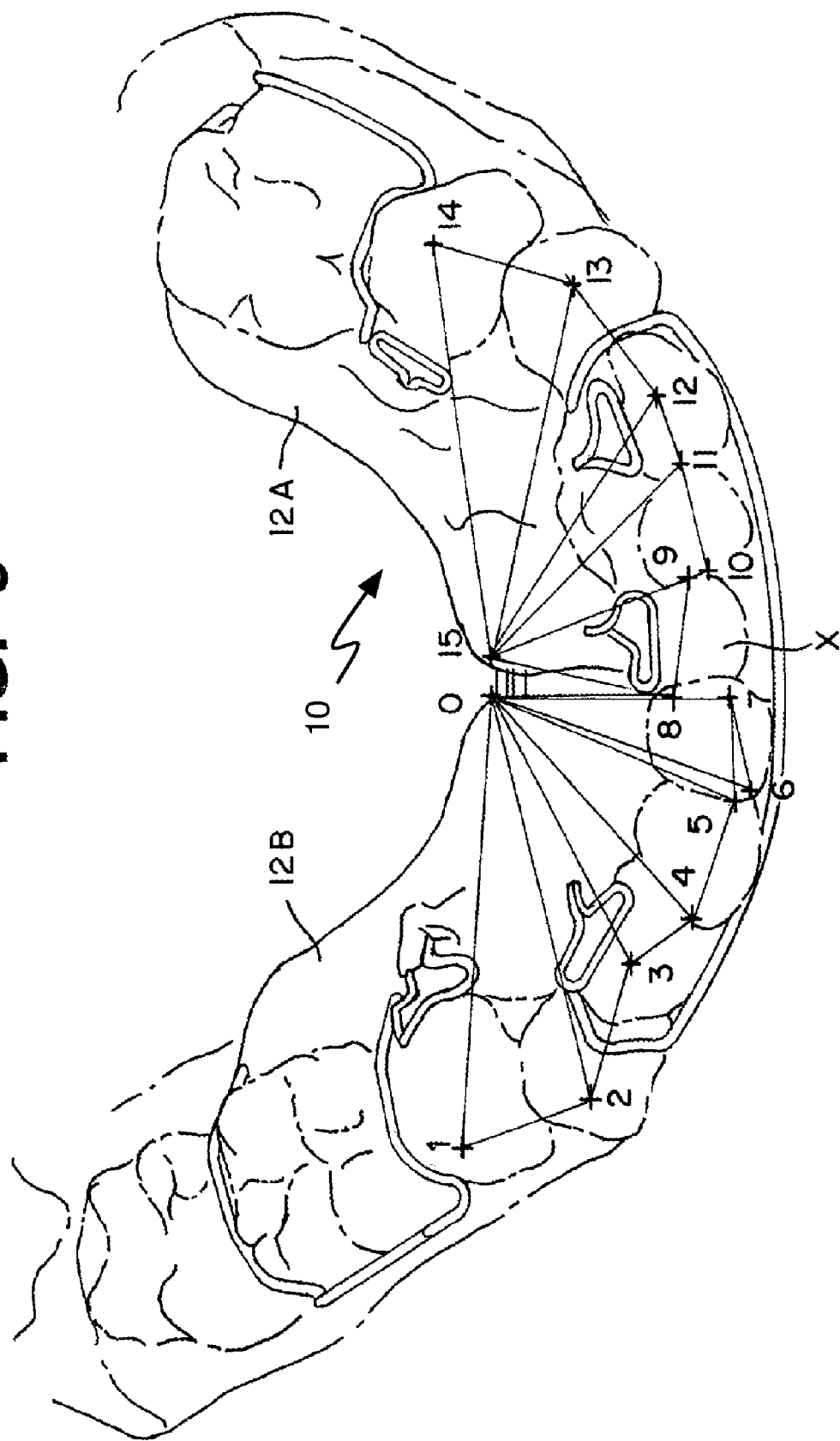
FIG. 5 is an illustration of the lower teeth in a patient's mouth at the beginning of treatment showing the placement of the device and a diagram of the alignment of the patient's teeth.
Figure 6:
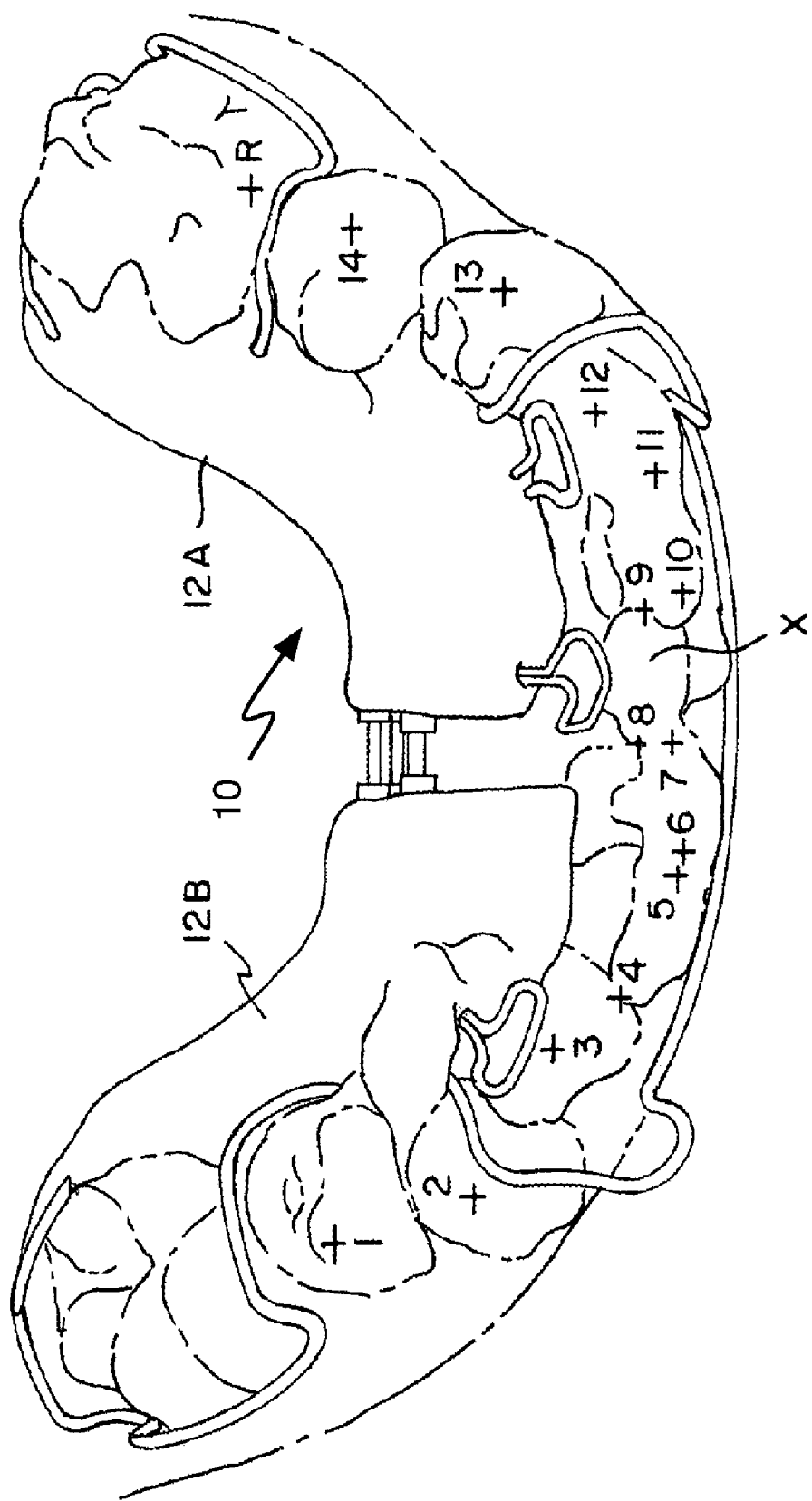
FIG. 6 is an illustration of the lower teeth in a patient's mouth after partial treatment showing the placement of the device and a diagram of the alignment of the patient's teeth at that point in the treatment.

FIG. 5 is a view of the teeth of a patient at the beginning of treatment showing the placement of the device and a diagram of the alignment of the patient's teeth. Notice that tooth X is out of alignment and there is not enough room between adjacent teeth for it to be properly aligned. FIG. 6 is similar to FIG. 5, but at a time after partial treatment of the patient. Notice that tooth X is now better aligned because more room has been provided between the adjacent teeth because of the effect of the device 10.

Marked on the illustration of FIG. 5 is a diagram of the alignment of the teeth. Using specific landmarks, reference lines (finite-elements) are drawn from location "0" on body plate half 12B and from location 15 on body plate half 12A to the teeth. The finite-elements are drawn to locations (landmarks) on the teeth, which are toward their front surfaces at about the mid points with regard to locations 1, 2, and 3 on body plate half 12B, as well as to locations 12, 13 and 14 on body plate half 12A. These represent teeth that are already in alignment. As regards the teeth to be aligned, similar finite-elements are drawn to the edges of each tooth, e.g., to locations 4,5 for one tooth and 6,7 for the other tooth from body plate 12B. Similarly, lines are drawn to locations 8,9 and 10,11 for the teeth contacted by the flap springs from plate body half 12A. Thus, specific landmarks are used to identify regions of the teeth and the device. By subjecting these specific landmarks to finite-element analysis, localization and quantification of changes in shape, size and direction of the spatial arrangements of the teeth and the device are computed, using a method developed by Singh et alia (Morphometry of the cranial base in subjects with Class III malocclusion. Journal of Dental Research, 76(2): 694-703, 1997).

Figure 7:
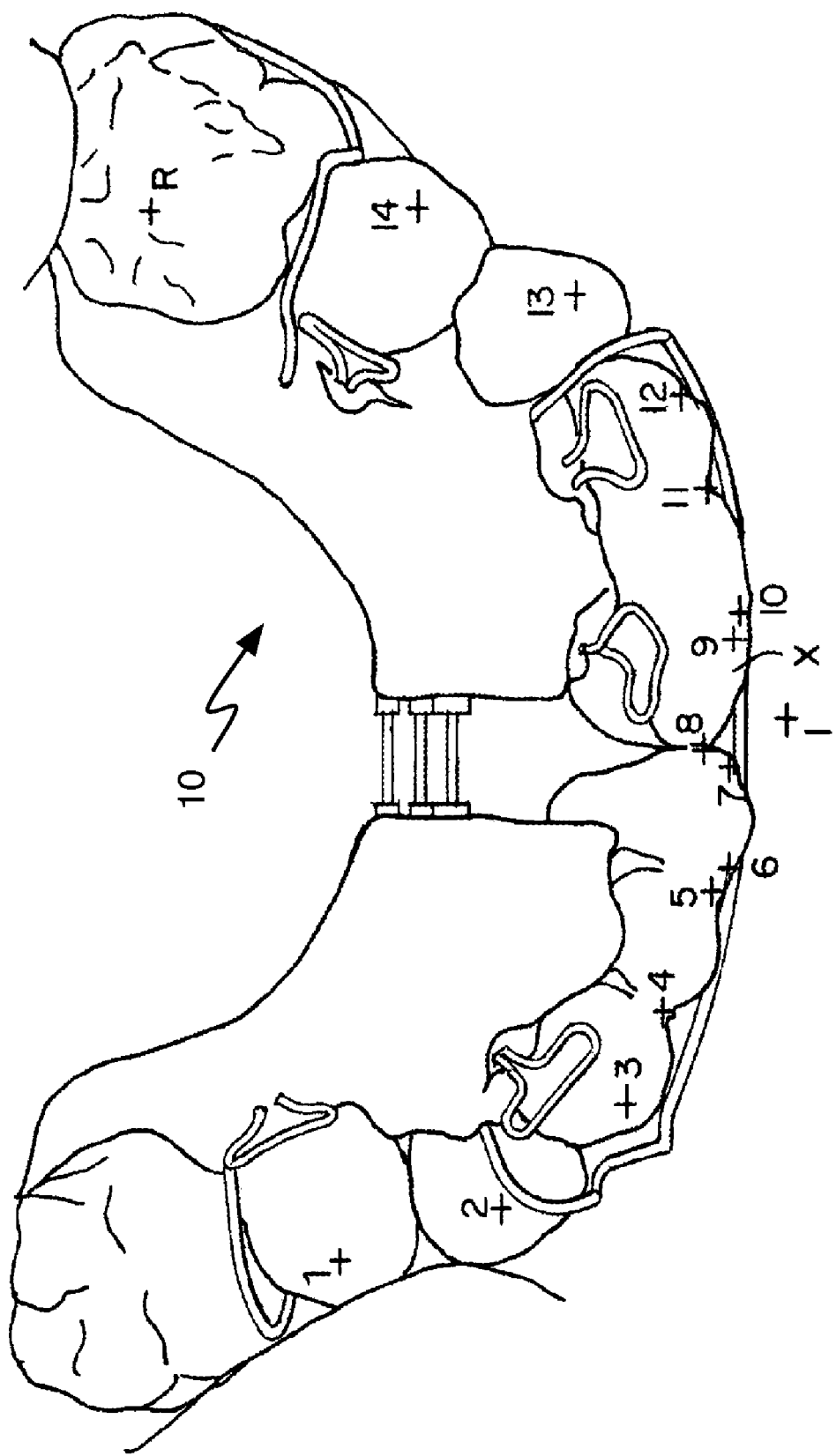
FIG. 7 is an illustration of the lower teeth in a patient's mouth near completion of treatment showing a diagram of the alignment of the patient's teeth at that point in the treatment.
Figure 8:
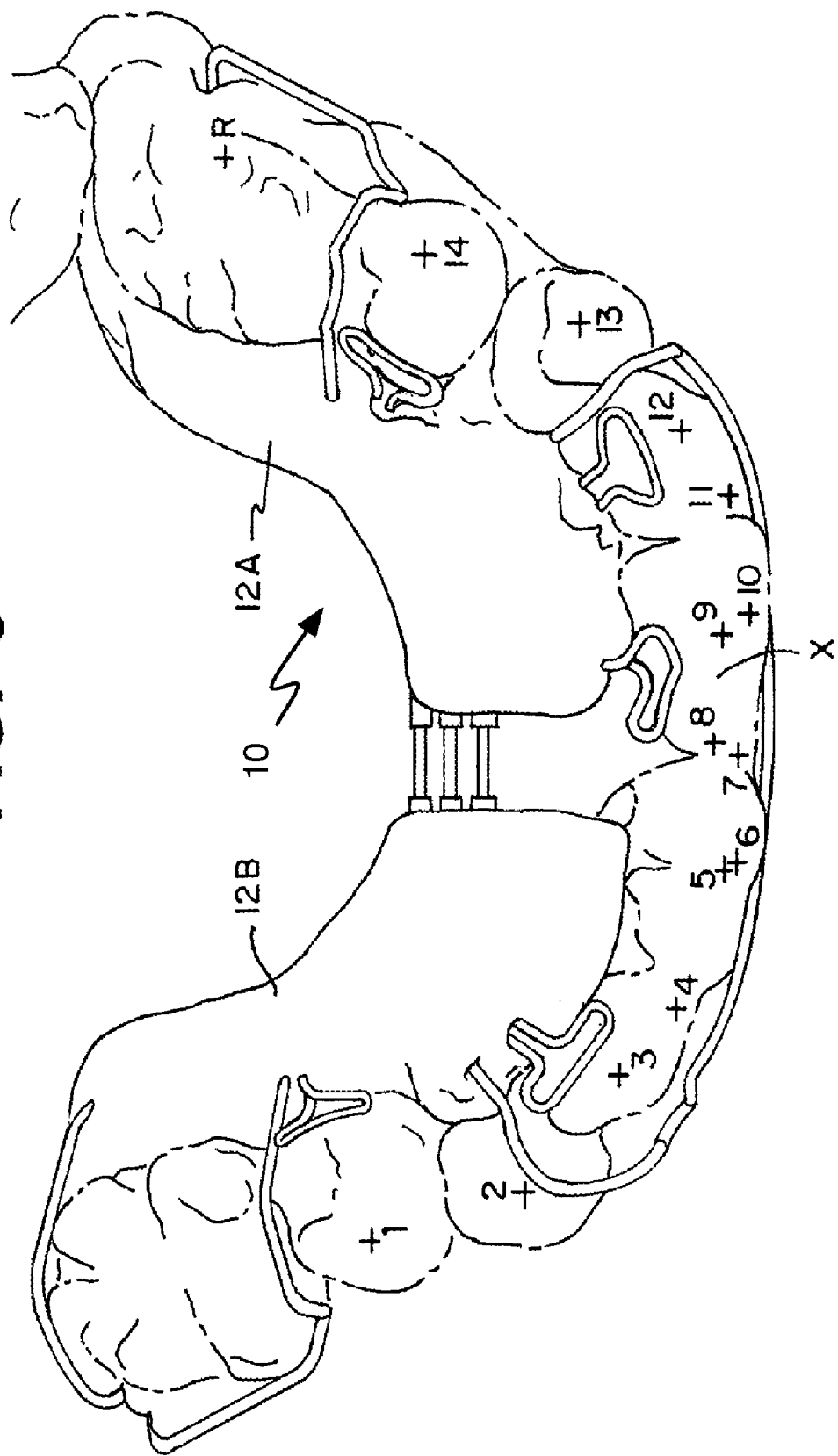
FIG. 8 is an illustration of the lower teeth in a patient's mouth after full treatment showing a diagram of the alignment of the patient's teeth at the end of treatment.
Figure 9:
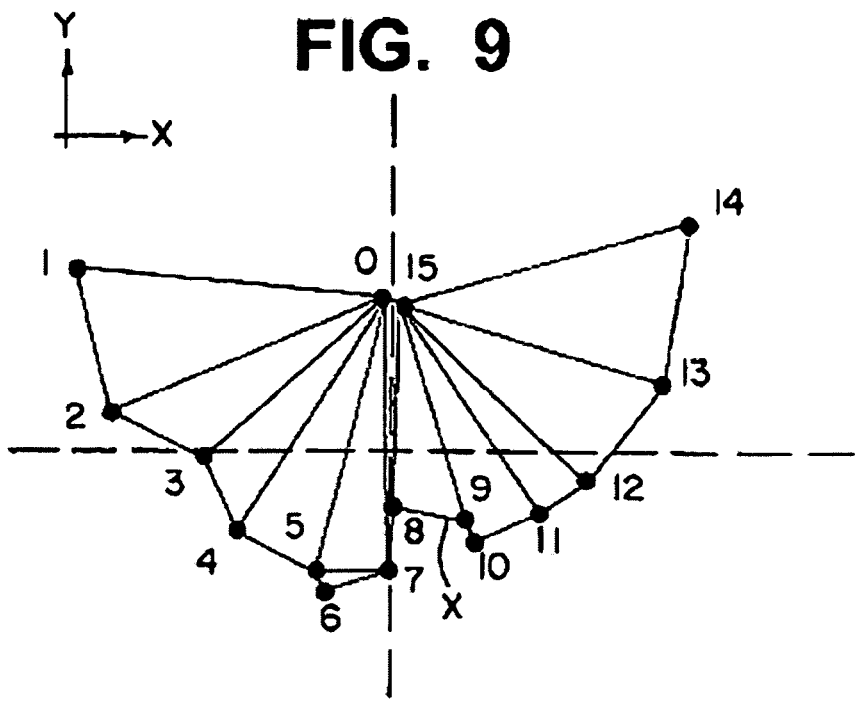
FIGS. 9-13 are diagrams of finite-elements of the teeth (dental arch) as marked in FIGS. 5-8 showing the progression of alignment of the teeth due to the device.
Figure 10:
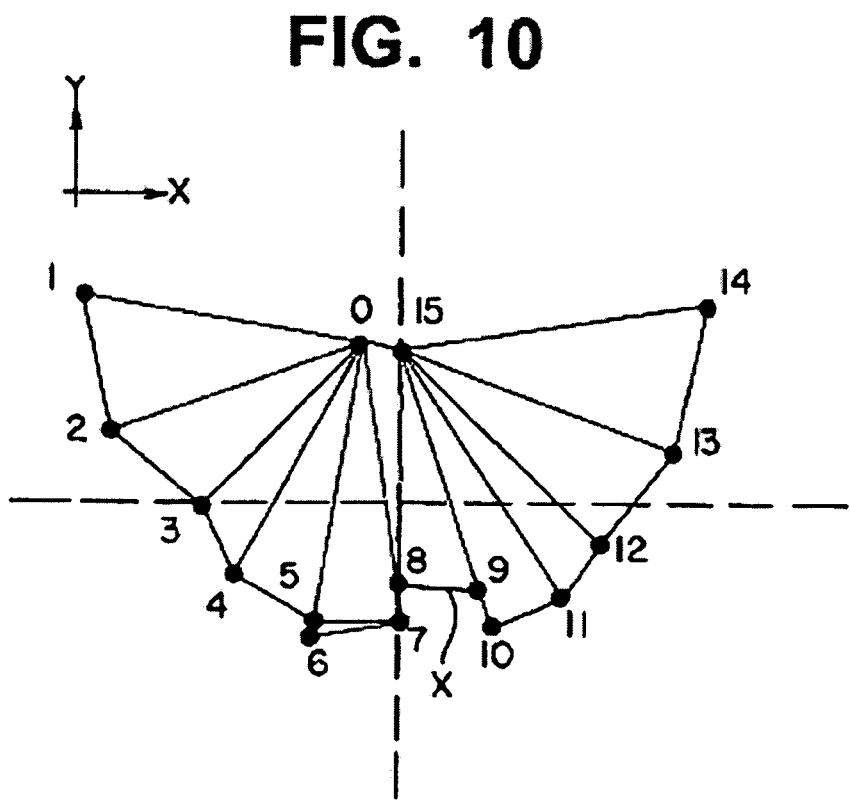
Figure 11:
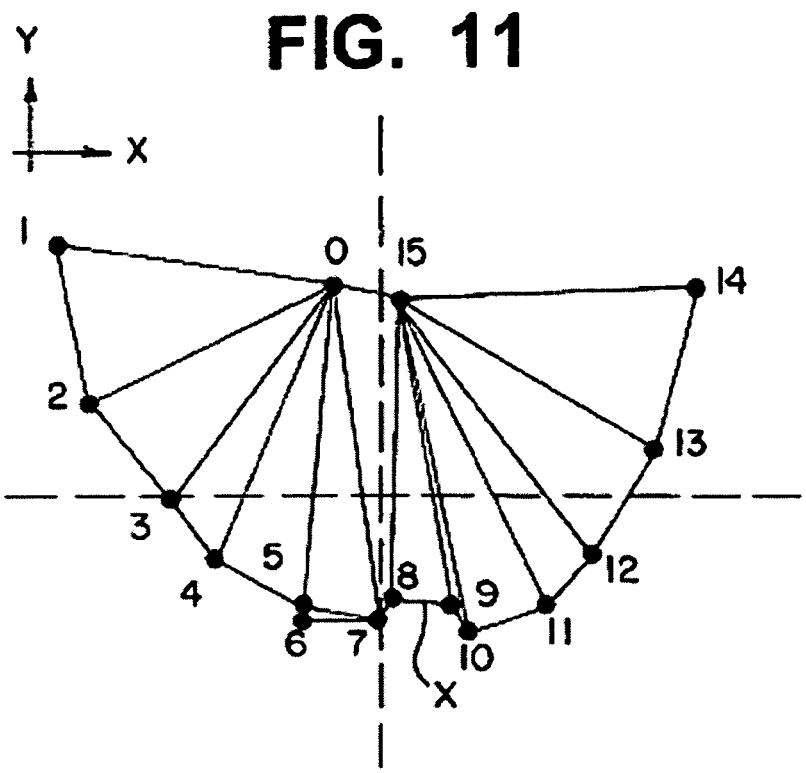
Figure 12:
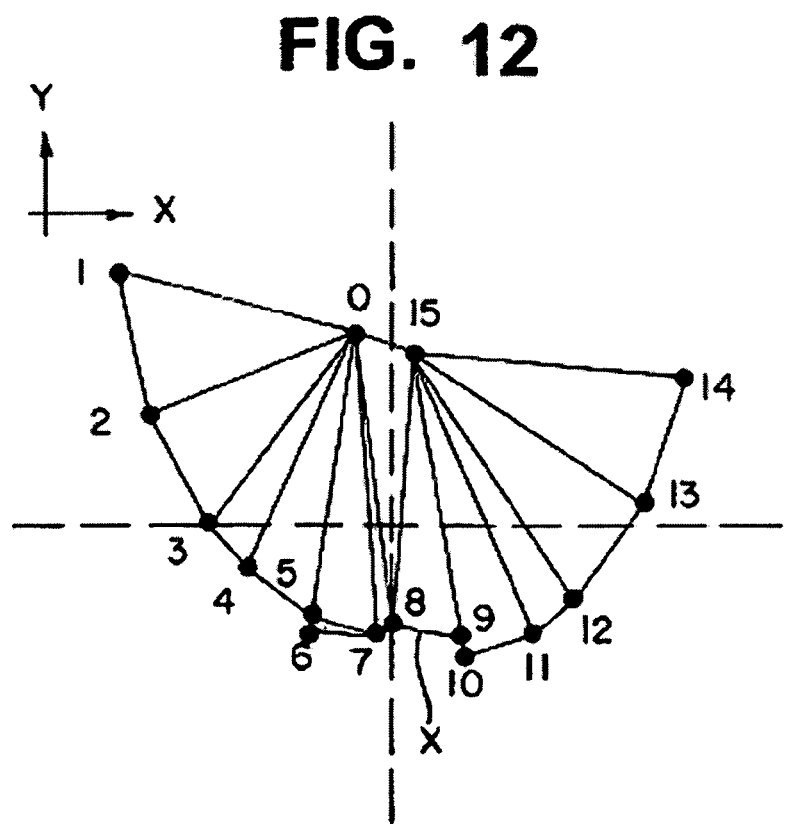
Figure 13:
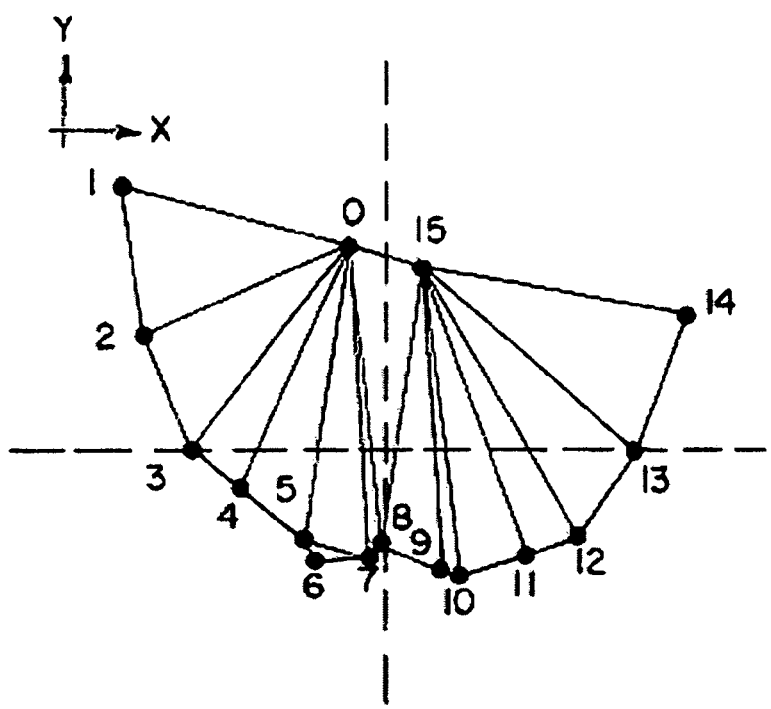

FIG. 7 shows the same patient about six (6) months later after wearing the device, essentially while sleeping approximately eight hours per night and for four waking hours per day. Notice that tooth X is nearly aligned. Finally, in FIG. 8 the arrangement of the teeth is shown at the end of treatment with tooth X properly aligned with the rest of the teeth. Throughout the process shown in FIGS. 6-8, the patient's jawbone has expanded in size, probably due to bone remodeling in the palatal region, and the teeth have been moved into new and properly aligned positions.

FIGS. 9-13 are diagrams of the teeth as marked in FIGS. 5-8 showing the progression of alignment of the teeth due to the device. These diagrams can be plotted in a graphics program such as MORPHOSTUDIO™, e.g., version 2.0 or higher. This set of diagrams particularly shows the movement of tooth X. As this response is typical of use of the invention, the diagrams of FIGS. 9-13 can be used to create a force profile, which would indicate the preferable force to be applied along each segment of the diagram at particular points in time in order to produce an acceptable result in the shortest period of time. When a microprocessor controlled device is used, this profile can be incorporated into the program of the microprocessor to apply force over time to the teeth in this manner.

Figure 16:
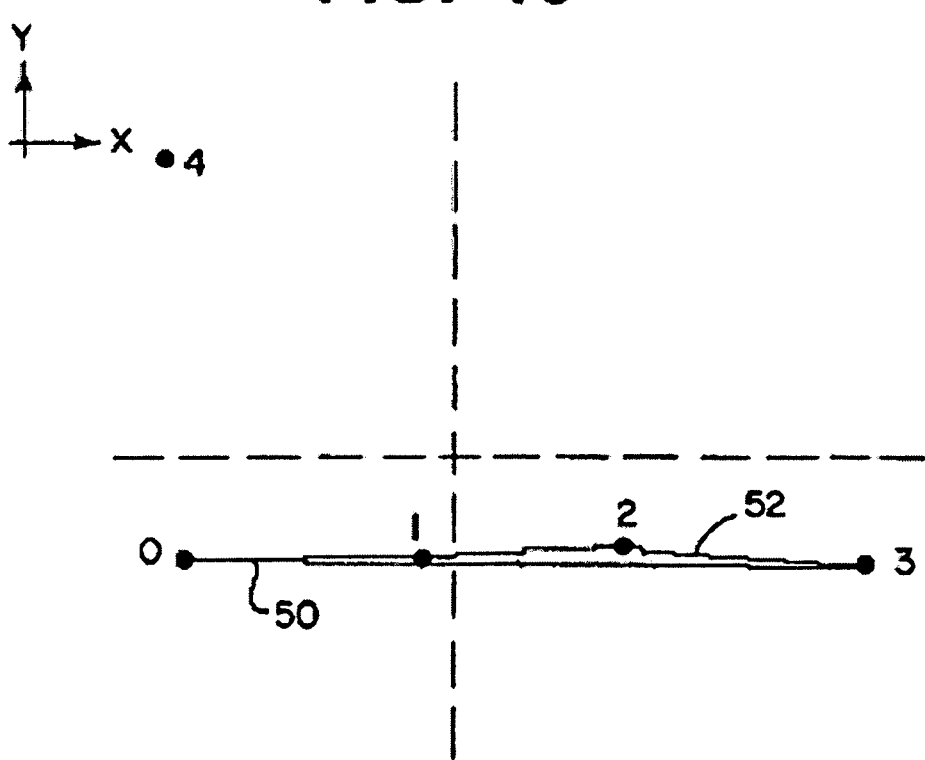
FIG. 16 is a diagram of the x, y coordinates of the eye alignment in FIG. 14 showing an under developed face.
Figure 14:
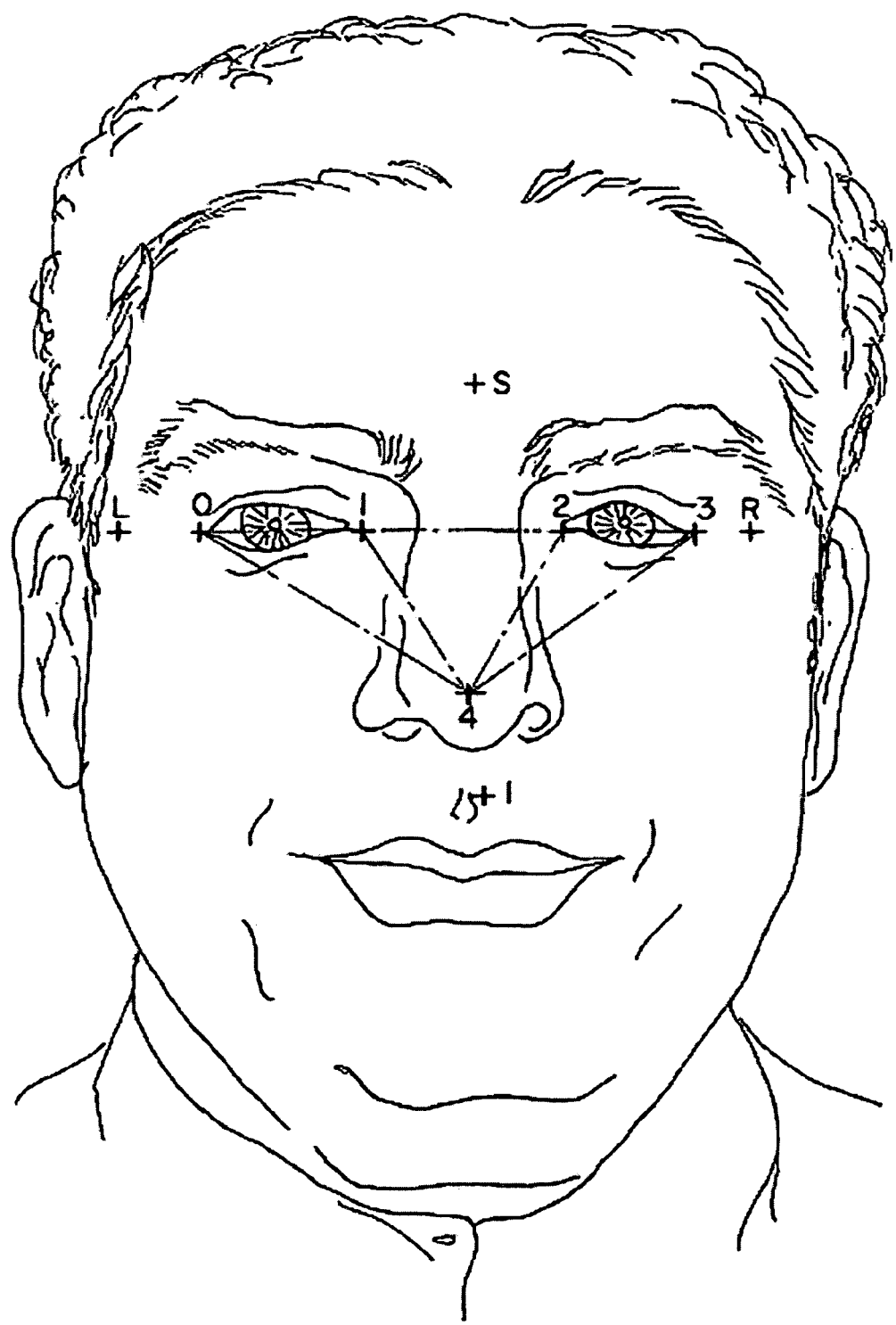
FIG. 14 is a reproduction of a photograph of a patient's face at the beginning of treatment showing a diagram of the alignment of the eyes.

FIG. 14 is an illustration of a patient's face at the beginning of treatment showing a diagram of the alignment of the eyes. Line 50 shows the alignment of the patient's eye on the left side of the illustration and line 52 shows the alignment of the patient's eye on the right side. The angle between the eyes is labeled 54. As can be seen, this angle 54 is noticeably less than 180 degrees, which would indicate perfect symmetry. FIG. 16 is a computer generated diagram of the lines 50, 52, which shows their relationship in more detail because the facial features are not present.

Figure 15:
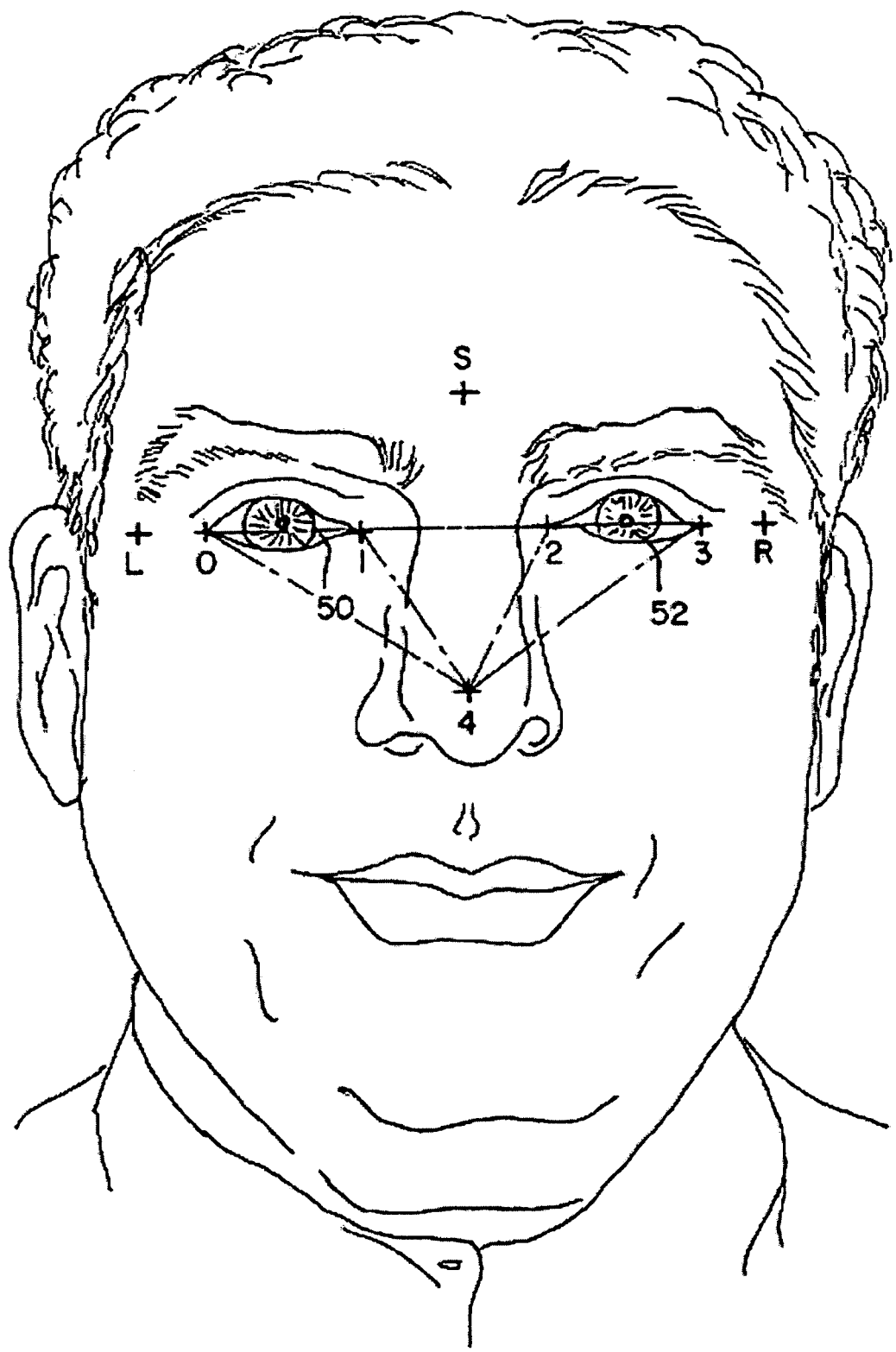
FIG. 15 is a reproduction of a photograph of the patient's face shown in FIG. 14 after full treatment showing a diagram of the alignment of the eyes and the symmetrical nature of the face.
Figure 17:
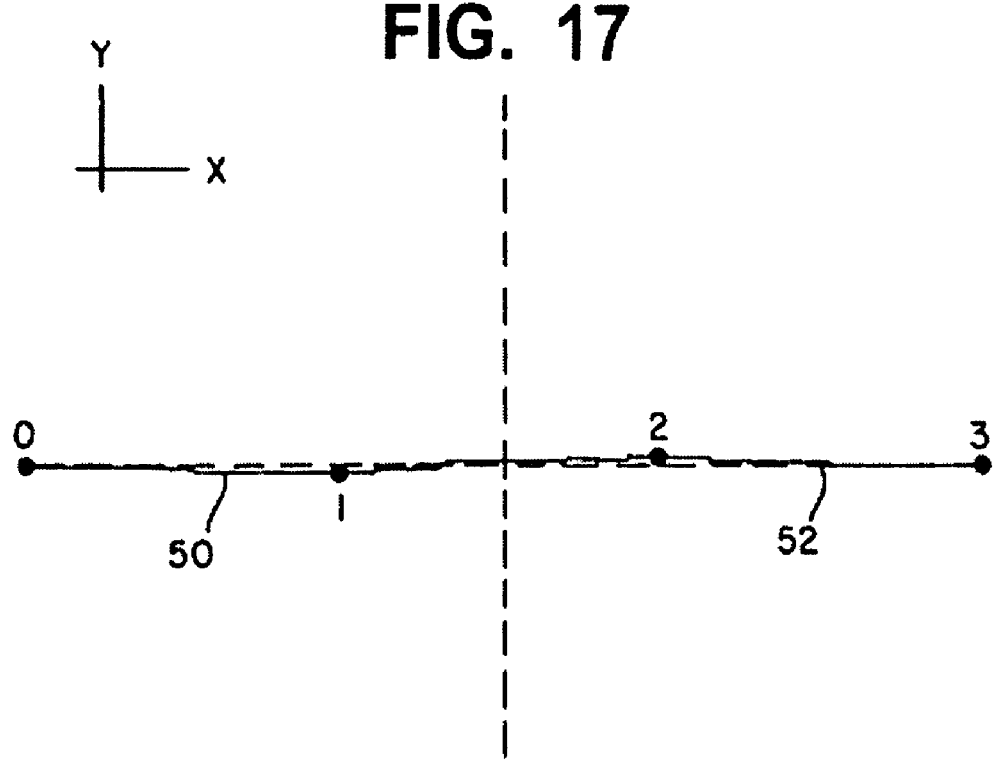
FIG. 17 is a diagram of the x, y coordinates of the eye alignment in FIG. 15, showing a developed symmetrical face.

FIG. 15 is an illustration of the face of the same patient shown in FIG. 14 after full treatment with the device according to the invention. As can be seen, the angle 54 is now almost 180 degrees, which indicates the alignment of the eyes and the symmetrical nature of the face. FIG. 17, which is a computer generated diagram of lines 50, 52 shows the alignment in more detail.

Figure 18:
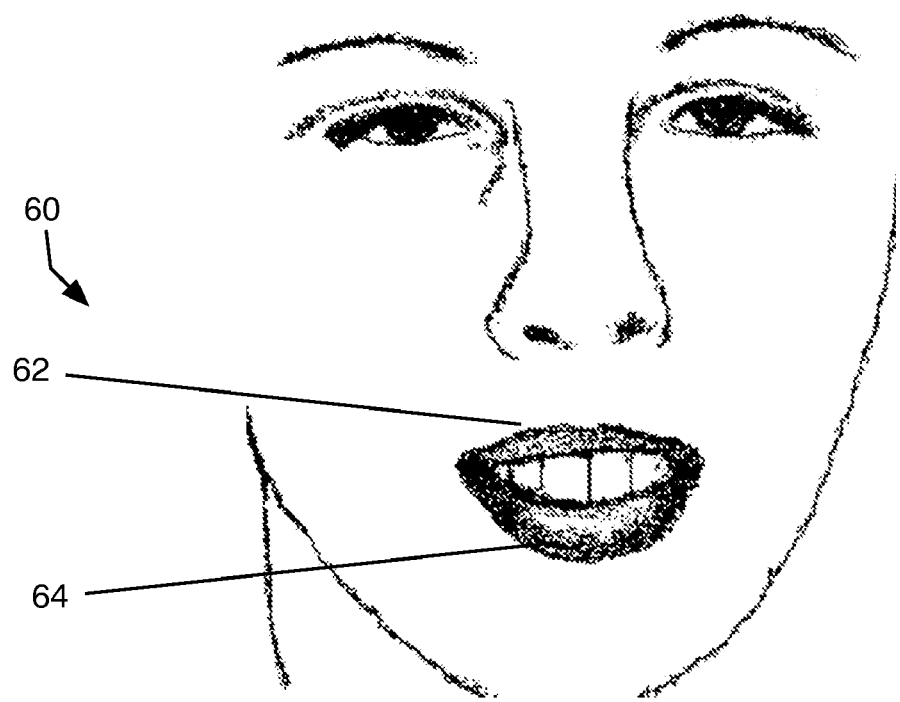
FIG. 18 is a reproduction of a photograph of a patient's face to show the lips before treatment with the device.
Figure 19:
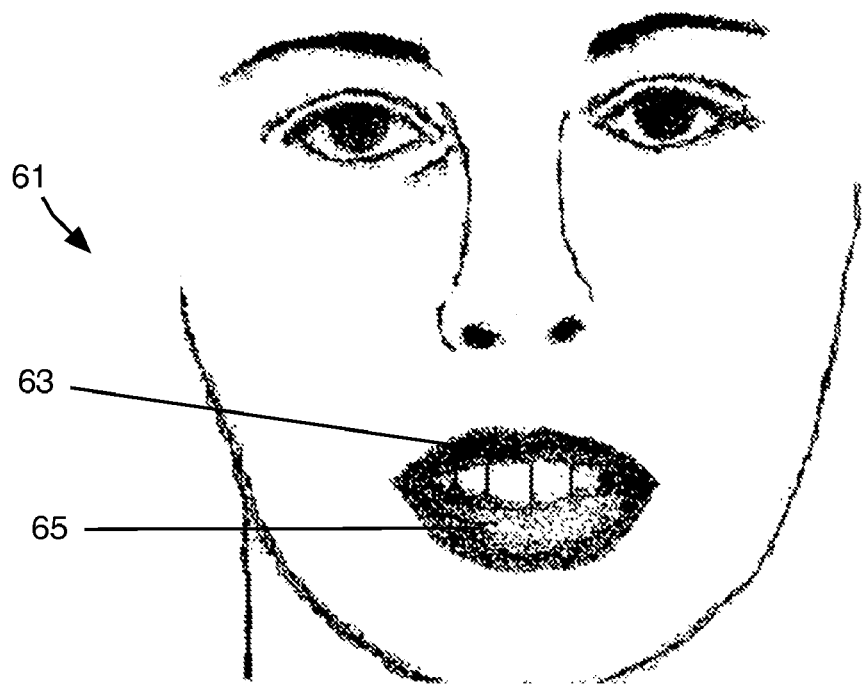
FIG. 19 is a reproduction of a photograph of the patient's face shown in FIG. 18 after full treatment with the device, showing the improvement in lip form.

FIGS. 18 and 19 are, respectively, reproductions of photographs of an individual's face 60, 61 before and after treatment with a device according to the present invention. In FIG. 18, before treatment, the individual's lips 62, 64 were thin and asymmetrical. The upper lip 62 was particularly thin. In FIG. 19, following treatment with a device of the present invention, the upper lip 63 and lower lip 65 are fuller and appear more symmetrical.

Figure 20:
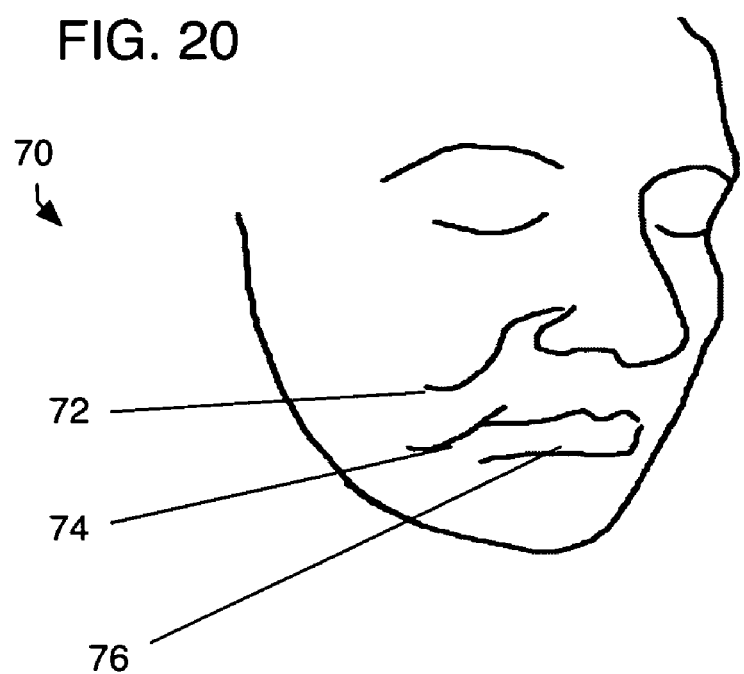
FIG. 20 is a reproduction of a photograph of a patient's face to show aging lines, sagging pouches and wrinkles on the face.
Figure 21:
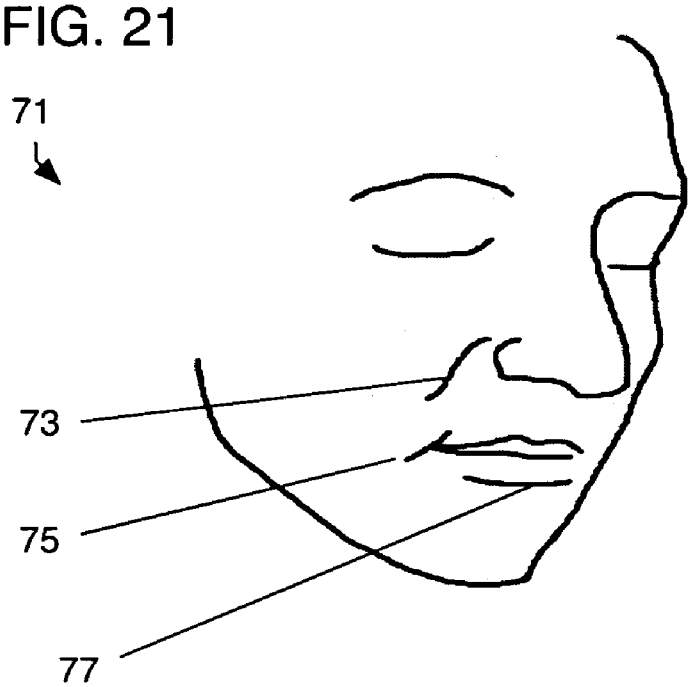
FIG. 21 is a reproduction of a photograph of the patient's face shown in FIG. 20 after full treatment with the device, showing the improvement in facial aging lines and reductions of sagging pouches and wrinkles on the face.

Referring now to FIGS. 20 and 21, reproductions of photographs of an individual's face 70, 71 are shown before (FIG. 20) and after (FIG. 21) treatment with a device of the present invention. Before treatment, aging lines 72, sagging pouches 74, and wrinkles 76 are prominent. After treatment, the degree and prominence of aging lines 73, sagging pouches 75, and wrinkles 77 are reduced, attributable to facial development, resulting in an increase in facial volume as described above.

Figure 22:
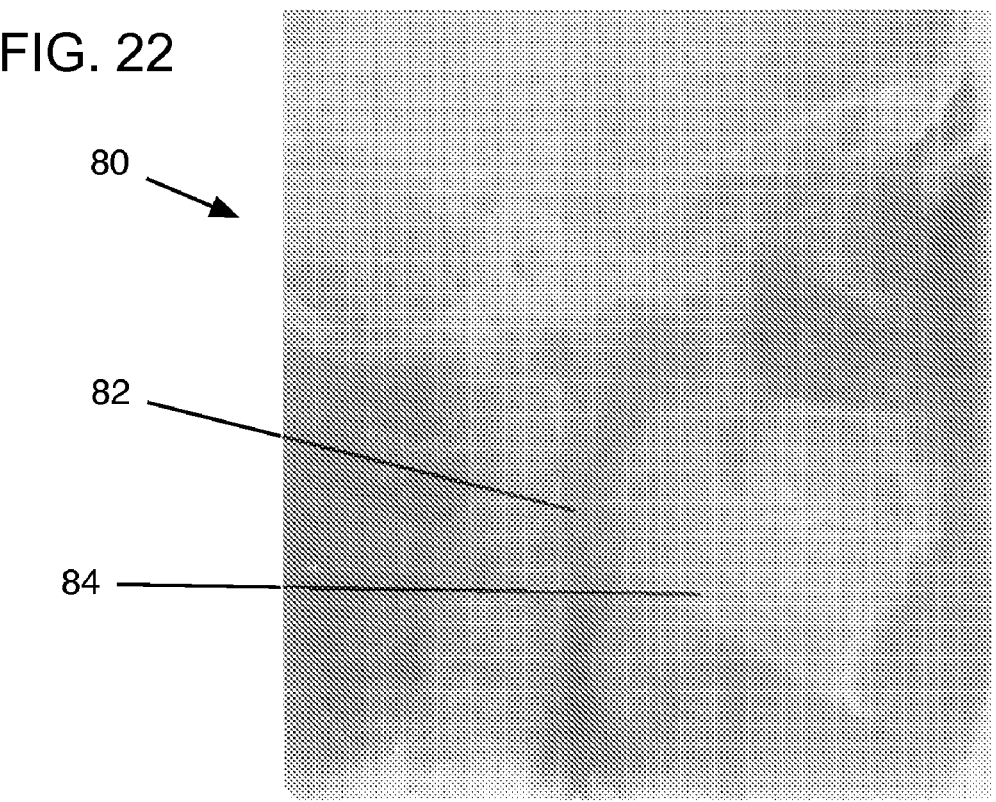
FIG. 22 is an x-ray showing the airway of a patient before treatment with the device from a side view.
Figure 23:
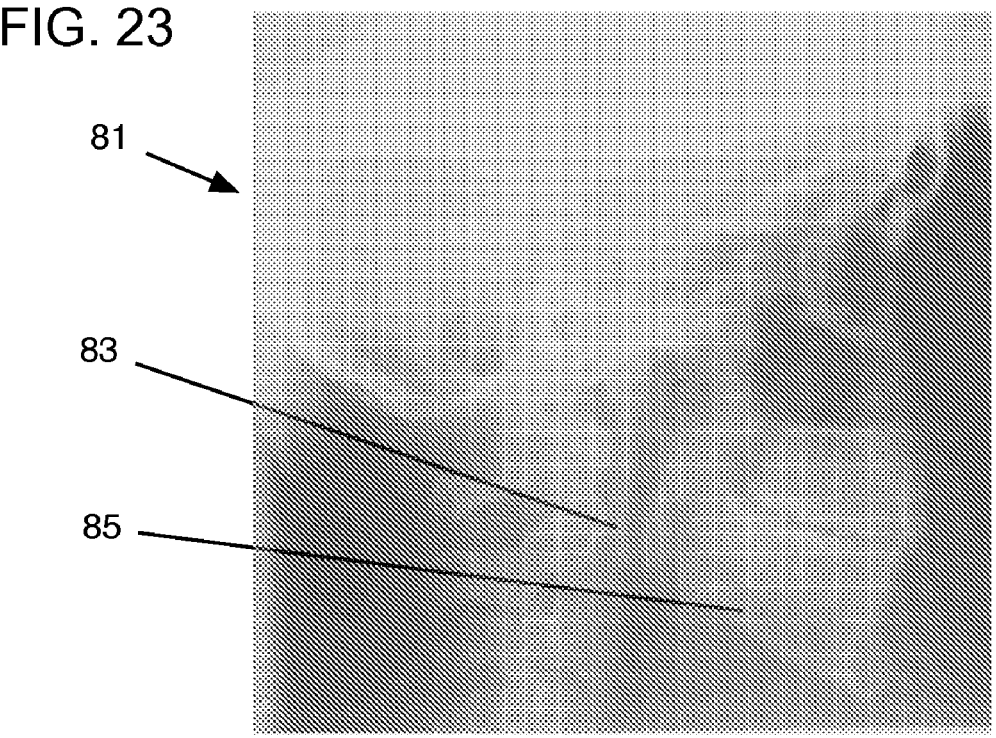
FIG. 23 is an x-ray of the patient in FIG. 22 showing the improvement in airway from a side view after treatment with the device.

FIGS. 22 and 23 are side view X-ray images of an individual's head and neck 80, 81 before (FIG. 22) and after (FIG. 23) treatment with a device of the present invention. Before treatment, the individual's airway 82 behind the jaw 84 is noticeably restricted and narrow. After treatment, the airway 83 behind the jaw 85 is opened and is much wider. Such improvements in an individual's airway may lead to, inter alia, reduced snoring, reduced sleep apnea, a better vocal quality, particularly vocal resonance, and increased longevity due to decreased oxidative stress.

In each of FIGS. 5-23, it can be seen that the use of device 10 caused a remodeling or reshaping of the bones and muscles of the face and jaw, thereby creating better facial symmetry. This remodeling may result, inter alia, in leveling of the eyes, higher cheekbones, stronger jaw appearance, and a wider smile, facial features that society usually equates with a pretty or handsome face. In addition, due to the functional nature of the appliance, improvements in the airway of the patient can be expected, as well as other more subtle improvements, such as improvement in lip shape, reduction of the dark shadows under the eyes, sinus decongestion, voice enhancement, decreased jaw-joint pain, decreased headaches, etc.

These enhancements were brought about by the application of intermittent force to the tissues of the face. During function, e.g., as the patient swallows while wearing the device, either while asleep or awake, the teeth come into contact with the overlay 14, which opens the bite, applies gentle forces to the face muscles, and signals the genes of the bones of the jaw through the device. These intermittent, cyclic, repetitive signals cause imperceptible deformations of the bones of the jaw and face, especially at bony joints called sutures. While not wishing to be held to any theory of operation, it is believed that the symmetrical nature of the result of the reformation of the jaw and facial bones is not due entirely to the application of force to specific areas of bone, but to the genetic code of the patient as predicted by the functional matrix hypothesis of Moss, and subsequent research which suggests that dormant genes can be evoked, expressed or re-expressed, or active genes can be switched off or otherwise modulated in non-growing adults.

Figure 24:
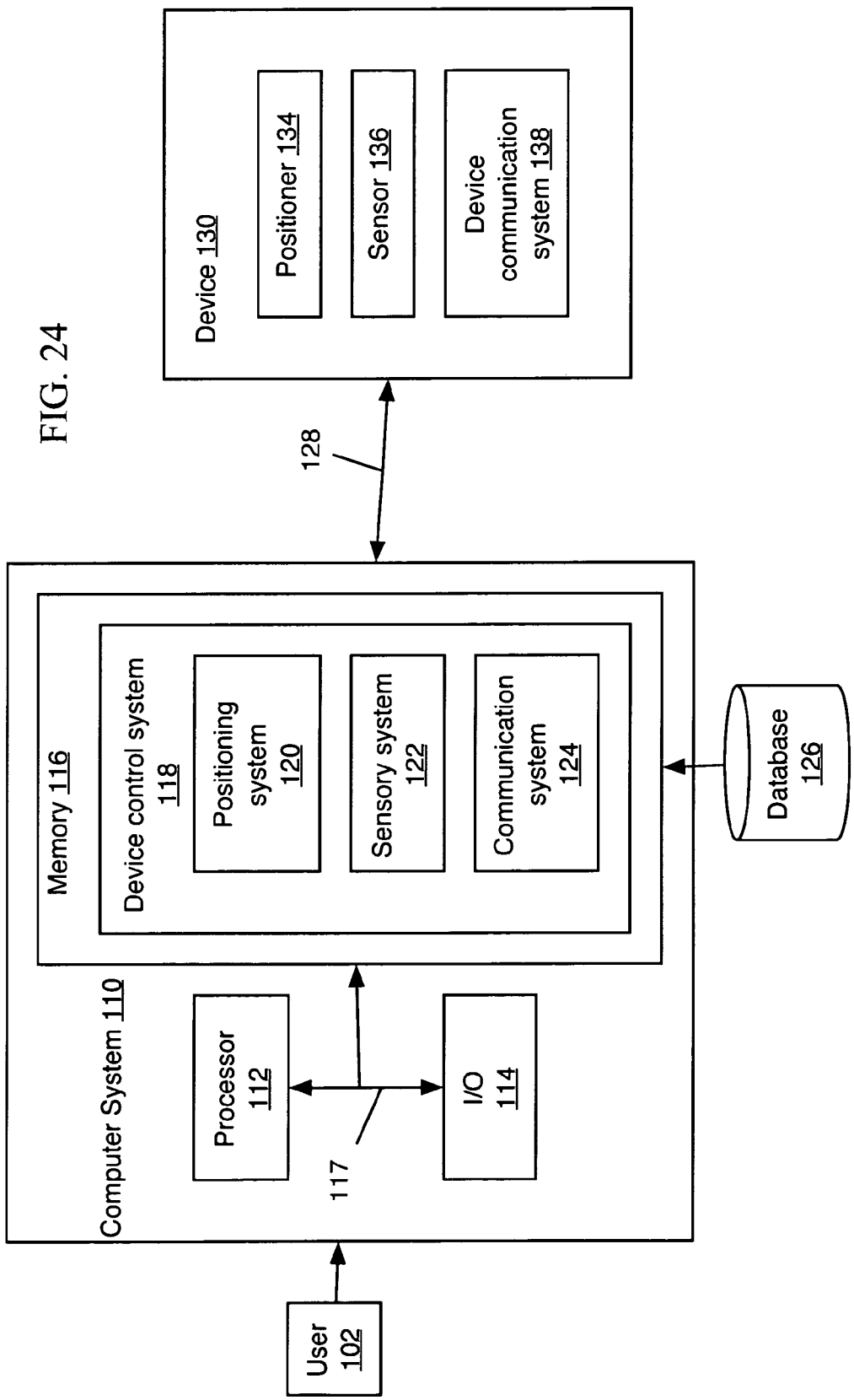
FIG. 24 is a block diagram of a computer system for controlling a device of the present invention.

Referring to FIG. 24, a block diagram is shown comprising a computer system 110 for controlling and/or monitoring a device 130 of the present invention. In general, computer system 110 may comprise, e.g., a desktop, a laptop, a workstation, etc. Moreover, computer system 110 could be implemented as part of a client and/or a server. Computer system 110 generally includes a processor 112, input/output (I/O) 114, memory 116, and bus 117. The processor 112 may comprise a single processing unit, or be distributed across one or more processing units in one or more locations, e.g., on a client and server. Memory 116 may comprise any known type of data storage and/or transmission media, including magnetic media, optical media, random access memory (RAM), read-only memory (ROM), a data cache, a data object, etc. Moreover, memory 116 may reside at a single physical location, comprising one or more types of data storage, or be distributed across a plurality of physical systems in various forms.

I/O 114 may comprise any system for exchanging information to/from an external resource. External devices/resources may comprise any known type of external device, including a monitor/display, speakers, storage, another computer system, a hand-held device, keyboard, mouse, voice recognition system, speech output system, printer, facsimile, pager, etc. Bus 117 provides a communication link between each of the components in the computer system 110 and likewise may comprise any known type of transmission link, including electrical, optical, wireless, etc. Although not shown, additional components, such as cache memory, communication systems, system software, etc., may be incorporated into computer system 110.

Access to computer system 110 may be provided over a network 128 such as the Internet, a local area network (LAN), a wide area network (WAN), a virtual private network (VPN), etc. Communication could occur via a direct hardwired connection (e.g., serial port), or via an addressable connection that may utilize any combination of wireline and/or wireless transmission methods. Moreover, conventional network connectivity, such as Token Ring, Ethernet, WiFi or other conventional communications standards could be used. Still yet, connectivity could be provided by conventional TCP/IP sockets-based protocol. In this instance, an Internet service provider could be used to establish interconnectivity. Further, as indicated above, communication could occur in a client-server or server-server environment.

Computer system 110 may receive data from a sensor 136 of device 130. As described above, data from sensor 136 may include information regarding a pressure exerted on a flap spring 28, a distance between portions of the plate body 12, a position of one or more device components, etc. Such data may be provided from device communication system 138 to communication system 124 on computer system 110. Sensory system 122 receives the sensor data and may determine whether a position of one or more device components should be adjusted. If such adjustment is desired, positioning system 120 may return data to device 130 through communication system 124 and device communication system 138, whereby positioner 134 repositions a device component such as a flap spring 28 or a portion of plate body 12, as described above. Device communication system 138 may include, for example, a microprocessor or the like.

A user 102 may interface with any function of device control system 118, including positioning system 120, sensory system 122, and communication system 124. Such interface may include, for example, the inputting of predetermined parameters for the functioning of device control system 118.

In addition, a database 126 may be included for storing data collected by computer system 110 and/or data provided to device 130. Such data may be that collected from or provided to one or more devices of the present invention.

It should be appreciated that the teachings of the present invention could be offered as a business method on a subscription or fee basis. For example, a computer system 110 comprising a device controlling system could be created, maintained and/or deployed by a service provider that offers the functions described herein for customers. That is, a service provider could offer to provide device monitoring and/or adjustment as described above.

It is understood that the systems, functions, mechanisms, methods, engines and modules described herein can be implemented in hardware, software, or a combination of hardware and software. They may be implemented by any type of computer system or other apparatus adapted for carrying out the methods described herein. A typical combination of hardware and software could be a general-purpose computer system with a computer program that, when loaded and executed, controls the computer system such that it carries out the methods described herein. Alternatively, a specific use computer, containing specialized hardware for carrying out one or more of the functional tasks of the invention could be utilized. In a further embodiment, part of all of the invention could be implemented in a distributed manner, e.g., over a network such as the Internet.

The present invention can also be embedded in a computer program product, which comprises all the features enabling the implementation of the methods and functions described herein, and which—when loaded in a computer system—is able to carry out these methods and functions. Terms such as computer program, software program, program, program product, software, etc., in the present context mean any expression, in any language, code or notation, of a set of instructions intended to cause a system having an information processing capability to perform a particular function either directly or after either or both of the following: (a) conversion to another language, code or notation; and/or (b) reproduction in a different material form.

Having described the presently preferred exemplary embodiment of an orthopedic and orthodontic device in accordance with the present invention, it is believed that other modifications, variations and changes will be suggested to those skilled in the art in view of the teachings set forth herein. It is, therefore, to be understood that all such modifications, variations, and changes are believed to fall within the scope of the present invention as defined by the appended claims.

What is claimed is:

1. A method for changing in an individual at least one craniofacial feature selected from a group consisting of an osteological feature, a dental feature, an anatomical feature, or a cosmetic feature, the method comprising the steps of:
   providing a device having a plate body that fits within the mouth of the individual, a flap spring that projects from the plate body, and an overlay extending from the plate body;
   placing the device within the mouth of the individual so that the overlay is in a position between at least an upper and lower tooth of the individual, the flap spring presses against at least one selected tooth that is out of place, and the plate body is spaced from the individual's tissues, including the palate; and
   arranging the shape and placement of the device such that contact of the individual's upper tooth and lower tooth or teeth with the overlay causes the individual's facial muscles to intermittently pull on at least one facial bone when the individual swallows, thereby causing a change in a craniofacial feature,
   wherein the anatomical feature is at least one of the form of an airway space behind the jaws, the form of the nose, the form of the nasal passages, the form of the sinuses, or the quality of the voice.

2. The method of claim 1, wherein the osteological feature is at least one of the form of at least one of the facial and jaw bones in which such bone did not develop fully during childhood, the form of the cheekbones in which such cheekbones did not develop fully during childhood, or the function of a jaw joint.

3. The method of claim 1, wherein the dental feature is the alignment of at least one tooth.

4. The method of claim 1, wherein the cosmetic feature is at least one of the alignment of the eyes, the presence of dark shadows below a lower eyelid, the symmetry of the lips, the thickness of a lip, the presence of lines in the face, or the sagging of facial skin.

5. The method of claim 1, wherein the placing step includes placing the overlay only between teeth on one side of the individual's mouth.

6. The method of claim 5, wherein the overlay is placed on the side of the individual's mouth where at least one facial bone did not fully develop during childhood.

7. The method of claim 1, wherein the placing step includes placing the overlay between teeth on both sides of the individual's mouth.

8. The method of claim 1, wherein the flap spring causes a jawbone to expand to accommodate movement of the at least one selected tooth.

9. The method of claim 1, wherein the plate body includes at least two pieces and at least one expansion screw therebetween.

10. The method of claim 9, further comprising the step of adjusting a space between the at least two pieces by operating the expansion screw.

11. The method of claim 10, wherein the expansion screw is operated by a motor.

12. The method of claim 10, wherein the device further includes at least one sensor for detecting at least one of a pressure applied to the selected tooth or a position of a component of the device.

13. The method of claim 12, further comprising the step of operating the expansion screw based on data from the at least one sensor.

14. The method of claim 12, wherein the device further includes a processor for collecting data from the at least one sensor.

15. The method of claim 14, wherein the expansion screw is operated by the processor based upon data from the at least one sensor and a predetermined parameter.

16. The method of claim 15, wherein the device further includes: a motor between the plate body and the at least one flap spring for controlling a pressure applied by the flap spring to the at least one selected tooth and at least one sensor for detecting a pressure applied to the at least one selected tooth.

17. The method of claim 16, further comprising the step of causing the processor to operate at least one of the expansion screw and the motor between the plate body and the flap spring.

18. The method of claim 17, wherein the causing step is performed remotely via a wireless transmission.

19. The method of claim 1, wherein the device further includes a motor between the plate body and the at least one flap spring for controlling a pressure applied by the flap spring to the at least one selected tooth.

20. The method of claim 19, further comprising the step of operating the motor to adjust the pressure applied by the flap spring.

21. The method of claim 19, wherein the device further includes at least one sensor for detecting a pressure applied to the at least one selected tooth.

22. The method of claim 21, further comprising the step of operating the motor to adjust the pressure applied by the flap spring based on data from the at least one sensor.

23. The method of claim 1, wherein the arranging step results in a change in expression of at least one gene.

* * * * *